United States Patent
Kim et al.

(10) Patent No.: US 8,568,623 B2
(45) Date of Patent: Oct. 29, 2013

(54) TRIPHENYLAMINE DERIVATIVES AND ORGANIC PHOTOVOLTAIC CELLS INCLUDING THE DERIVATIVES

(71) Applicant: Korea Institute of Science and Technology, Seoul (KR)

(72) Inventors: Bong Soo Kim, Seoul (KR); Min Jae Ko, Seoul (KR); Hong Gon Kim, Seoul (KR); Jin Young Kim, Gyeonggi-do (KR); Hyo Sang Lee, Seoul (KR); Minwoo Jung, Gyeongsangnam-do (KR); Doh-Kwon Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/660,038

(22) Filed: Oct. 25, 2012

(65) Prior Publication Data

US 2013/0234075 A1    Sep. 12, 2013

(30) Foreign Application Priority Data

Mar. 8, 2012 (KR) ........................ 10-2012-0023964

(51) Int. Cl.
| | |
|---|---|
| F21V 9/00 | (2006.01) |
| G02B 5/02 | (2006.01) |
| G02C 7/10 | (2006.01) |
| G02F 1/361 | (2006.01) |
| G03B 11/00 | (2006.01) |
| H01L 31/00 | (2006.01) |
| C08F 128/06 | (2006.01) |
| C08F 134/04 | (2006.01) |
| C08F 228/06 | (2006.01) |
| C08F 234/04 | (2006.01) |
| C08F 28/06 | (2006.01) |
| C08F 34/04 | (2006.01) |

(52) U.S. Cl.
USPC ........... 252/582; 136/256; 136/263; 526/256; 526/259

(58) Field of Classification Search
USPC ............. 252/582; 257/40, E51.012, E51.018; 526/256, 259; 548/453; 136/256, 263
See application file for complete search history.

(56) References Cited

PUBLICATIONS

Yuze Lin, Pei Cheng, Yongfang Li and Xiaowei Zhan, A 3D star-shaped non-fullerene acceptor for solution-processed organic solar cells with a high open-circuit voltage of 1.18 V, Chem. Commun., 2012, 48, 4773-4775.*

*Primary Examiner* — Bijan Ahvazi
(74) *Attorney, Agent, or Firm* — Ladas & Parry LLP

(57) ABSTRACT

Disclose is a triphenylamine derivative with a low band gap. The triphenylamine derivative is represented by Formula (I):

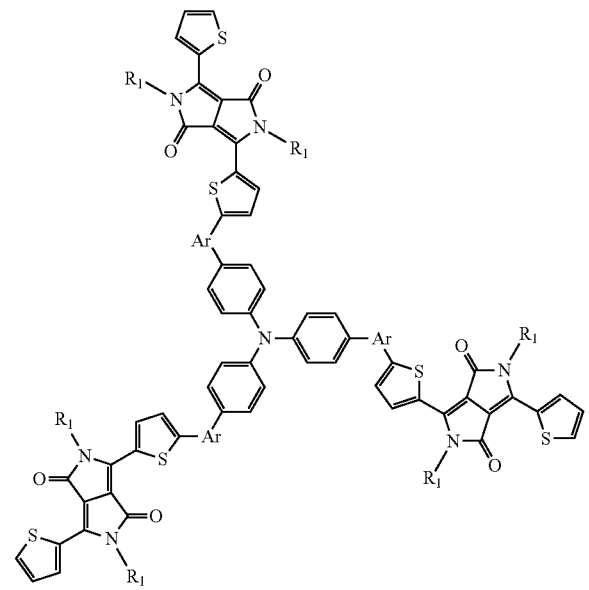

wherein $R_1$ and Ar are as defined in the specification. Further disclosed is a high efficiency organic photovoltaic cell using the derivative.

7 Claims, 2 Drawing Sheets

(56) References Cited

PUBLICATIONS

Duryodhan Sahu, Chia-Hua Tsai, Hung-Yu Wei, Kuo-Chuan Ho, Feng-Chih Chang and Chih-Wei Chu,Synthesis and applications of novel low bandgap star-burst molecules containing a triphenylamine core and dialkylated diketopyrrolopyrrole arms for organic photovoltaics,J. Mater. Chem., 2012, 22, 7945.*

Johan C. Bijleveld, Arjan P. Zoombelt, Simon G. J. Mathijssen, Martijn M. Wienk, Mathieu Turbiez,Dago M. de Leeuw, and Rene' A. J. Janssen, Poly(diketopyrrolopyrrole-terthiophene) for Ambipolar Logic and Photovoltaics,J. Am. Chem. Soc. 2009, 131, 16616-16617.*

Bright Walker, Arnold B. Tamayo, Xuan-Dung Dang, Peter Zalar, Jung Hwa Seo, Andres Garcia, Mananya Tantiwiwat, and Thuc-Quyen Nguyen, Nanoscale Phase Separation and High Photovoltaic Efficiency in Solution-Processed, Small-Molecule Bulk Heterojunction Solar Cells, Adv. Funct. Mater. 2009, 19, 3063-3069.*

Hsiang-Yu Chen, et al; "Polymer solar cells with enhanced open-circuit voltage and efficiency", Nature photonics, vol. 3, Published online Oct. 25, 2009, pp. 649-653.

Wanli Ma, et al; "Thermally Stable, Efficient Polymer Solar Cells with Nanoscale Control of the Interpenetrating Network Morphology", Advanced Functional Materials, vol. 15, Issue 10, pp. 1617-1622; Article first published online: Sep. 1, 2005.

Gang Li, et al; "High-efficiency solution processable polymer photovoltaic cells by self-organization of polymer blends", Nature Materials, vol. 4, Published online Oct. 9, 2005, pp. 864-868.

* cited by examiner

TRIPHENYLAMINE DERIVATIVES AND ORGANIC PHOTOVOLTAIC CELLS INCLUDING THE DERIVATIVES

CROSS-REFERENCE TO RELATED APPLICATIONS

This application claims priority under 35 U.S.C. §119 to Korean Patent Application No. 10-2012-0023964 filed on Mar. 8, 2012, in the Korean Intellectual Property Office, the disclosure of which is incorporated herein by reference in its entirety.

BACKGROUND OF THE INVENTION

1. Field of the Invention

The present invention relates to triphenylamine derivatives and a method for preparing the derivatives. More specifically, the present invention relates to triphenylamine derivatives with low band gaps and high efficiency organic photovoltaic cells using the derivatives.

2. Description of the Related Art

The supply of fossil fuels as representative energy sources is finite and the emission of carbon dioxide from the combustion of fossil fuels brings about environmental problems, such as greenhouse effect. Under these circumstances, there is a growing demand for environmentally friendly alternative energy sources. In efforts to overcome the problems of fossil fuels, various energy sources, such as water power and wind power, are being investigated, and the sunlight is also investigated as a new renewable energy source due to its unlimited availability. Solar powered photovoltaic cells can be broadly classified into two groups: photovoltaic cells using inorganic materials, such as silicon, and photovoltaic cells using organic materials. In comparison with silicon-based inorganic photovoltaic cells, organic thin-film photovoltaic cells have the advantages of low fabrication costs and the possibility of manufacturing freely bendable, flexible, large-area devices. Due to these advantages, a great deal of research has been conducted on organic thin-film photovoltaic cells. Most studies on materials for organic thin-film photovoltaic cells have focused on polymeric materials (G. Li, V. Shrotriya, J. S. Huang, Y. Yao, T. Moriarty, K. Emery and Y. Yang, *Nat. Mater.*, 2005, 4, 864-868, W. L. Ma, C. Y. Yang, X. Gong, K. Lee and A. J. Heeger, *Adv. Fund'. Mater.*, 2005, 15, 1617-1622, H.-Y. Chen, J. Hou, S. Zhang, Y. Hang, G. Yang, G. Yang, Y. Yang, L. Yu, Y. Wu, G. Li, *Nat. Photon.*, 2009, 3, 649). However, the control over the molecular weight of polymeric materials and the removal of catalysts are difficult. The efficiency of photovoltaic cell devices may vary depending on the arrangement of polymeric materials, resulting in poor reproducibility of performance. To overcome such drawbacks, there arises a need to develop a novel monomolecular compound that has a low band gap over a broad light-absorbing range, a high hole mobility and an appropriate molecular level, thus being suitable for use in the fabrication of a high efficiency organic photovoltaic cell.

SUMMARY OF THE INVENTION

It is an object of the present invention to provide triphenylamine derivatives with low band gaps suitable for use in organic photovoltaic cells, and a method for preparing the derivatives.

It is another object of the present invention to provide high efficiency organic photovoltaic cells including the triphenylamine derivatives with low band gaps.

According to an aspect of the present invention, there is provided a triphenylamine derivative represented by Formula (I):

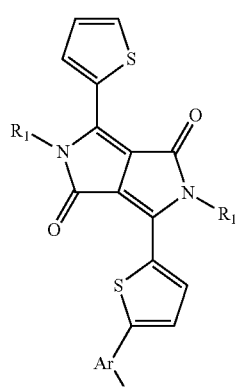

(I)

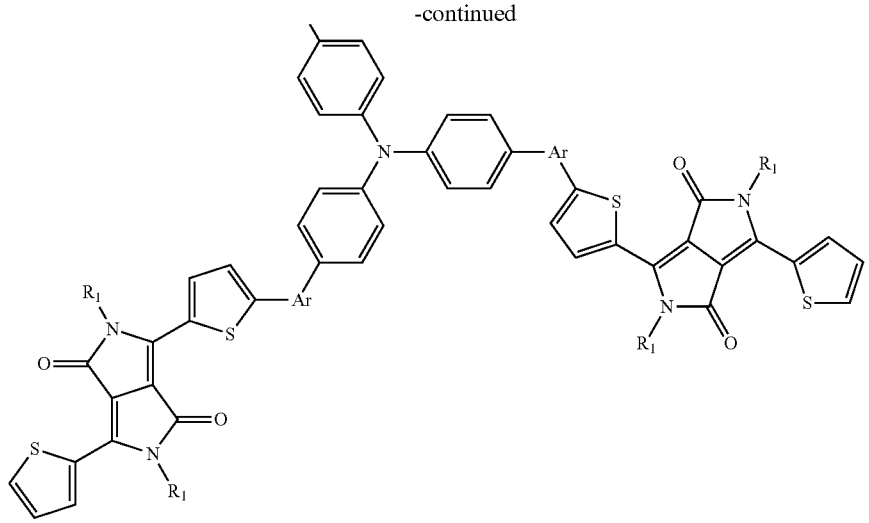

wherein the $R_1$ groups, which may be the same or different, each independently represent a straight or branched, saturated or unsaturated $C_1$-$C_{20}$ alkyl group, and the Ar moieties, which may be the same or different, each independently represent a linking group selected from

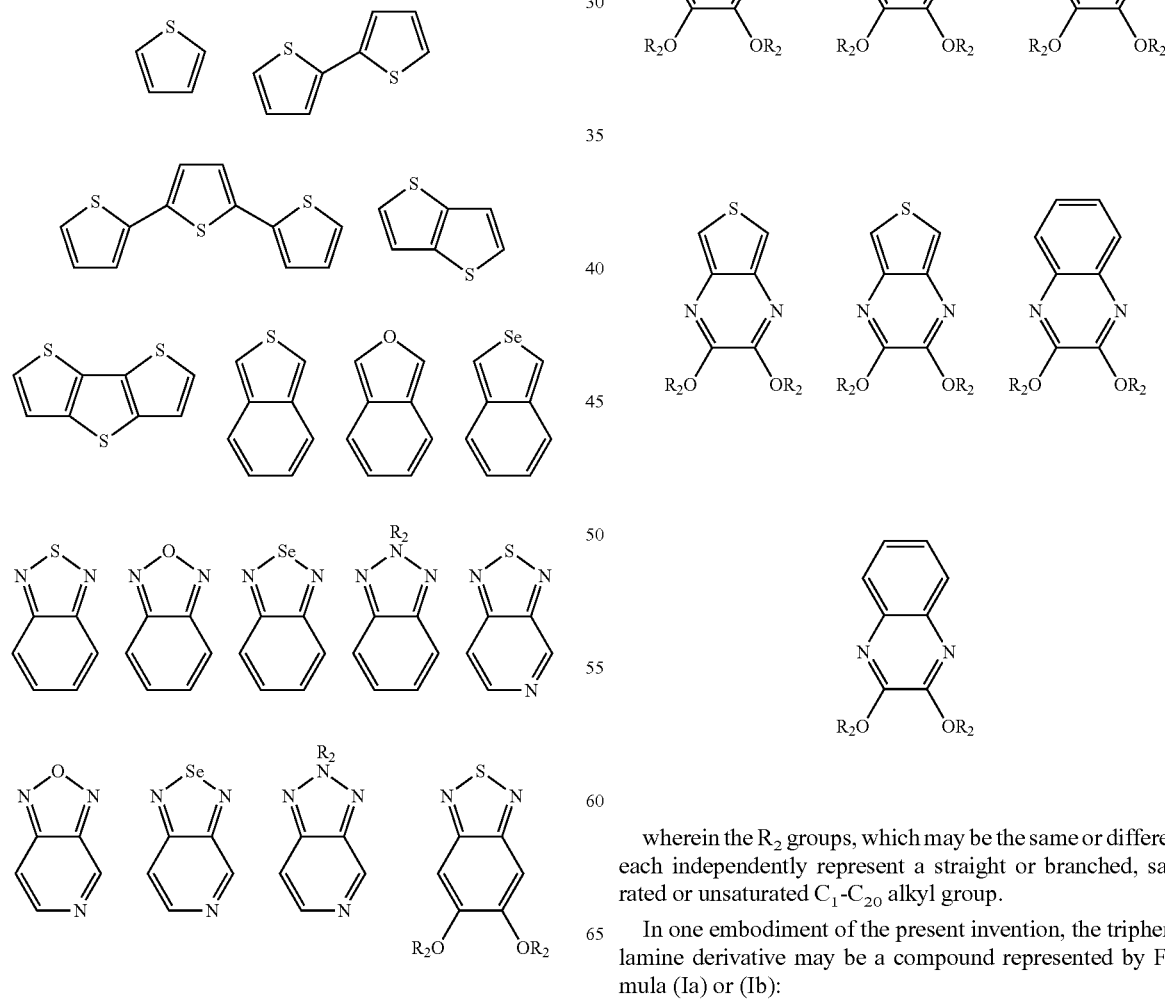

wherein the $R_2$ groups, which may be the same or different, each independently represent a straight or branched, saturated or unsaturated $C_1$-$C_{20}$ alkyl group.

In one embodiment of the present invention, the triphenylamine derivative may be a compound represented by Formula (Ia) or (Ib):

(Ia)
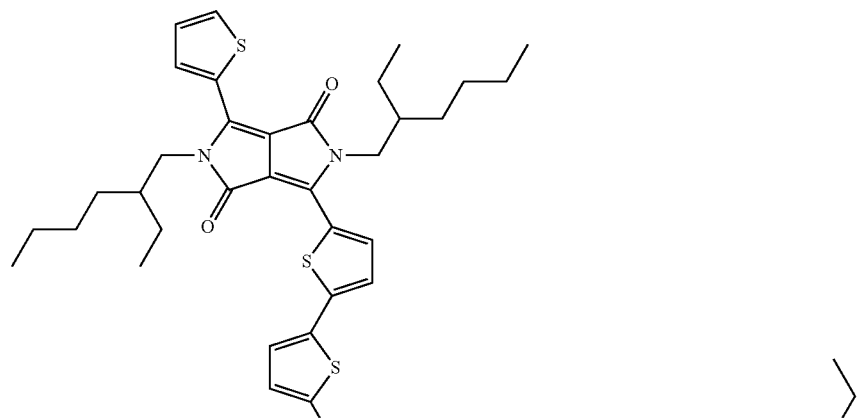
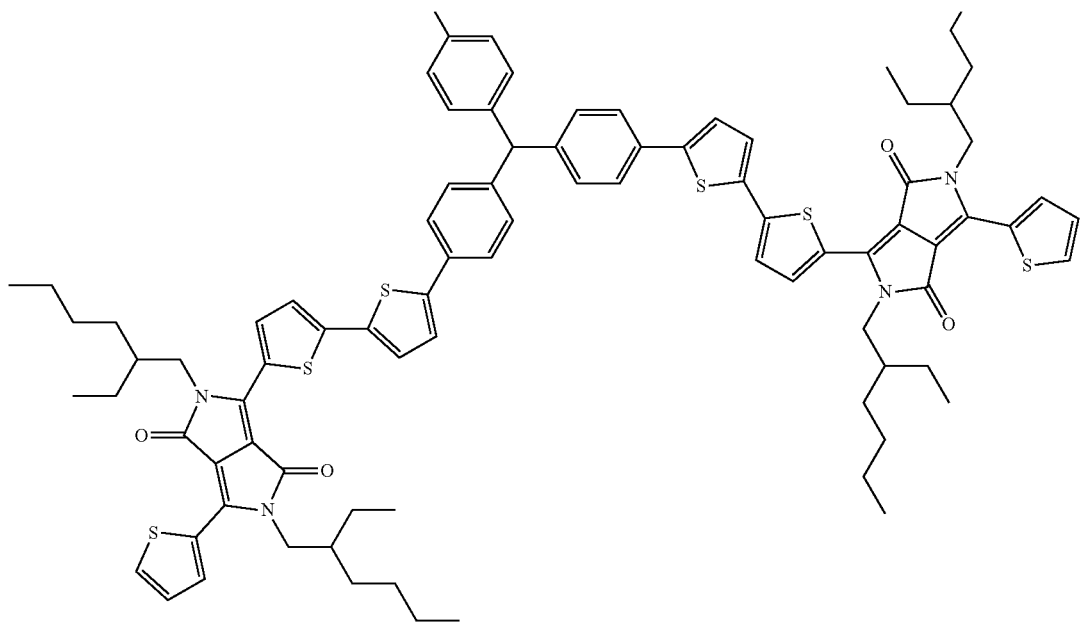
(Ib)
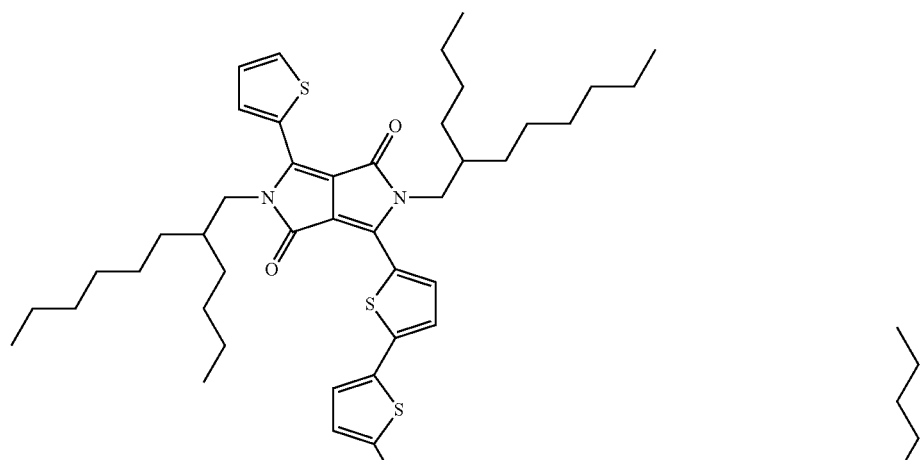

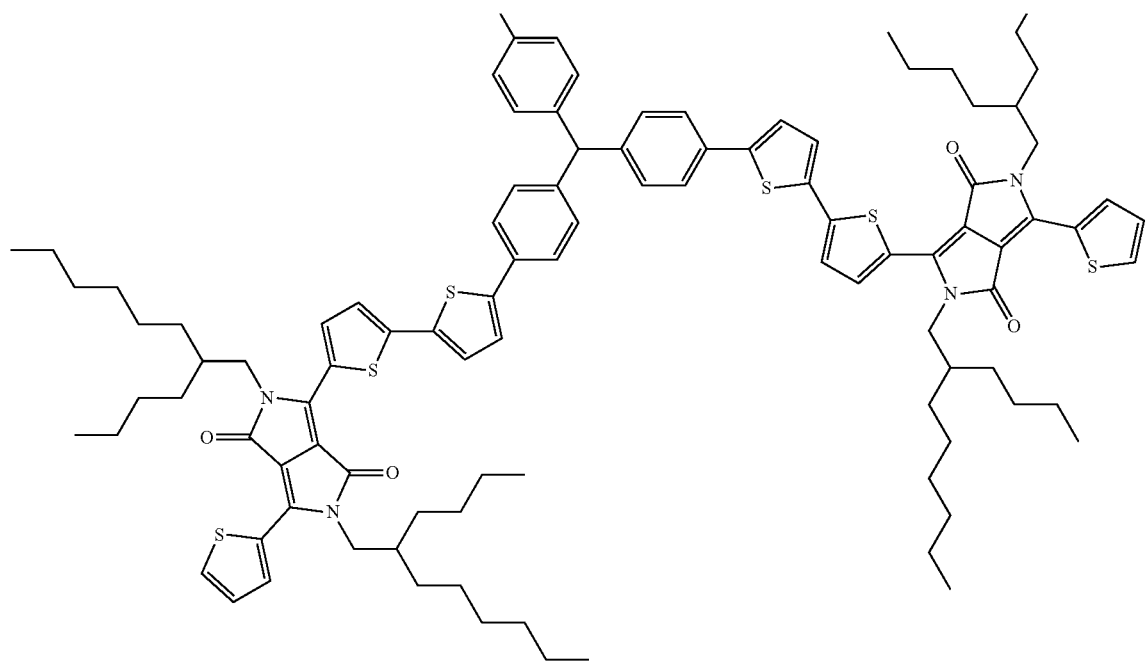
30
According to another aspect of the present invention, there is provided a method for preparing a triphenylamine derivative represented by Formula (I), as depicted in Reaction (I):
(I)
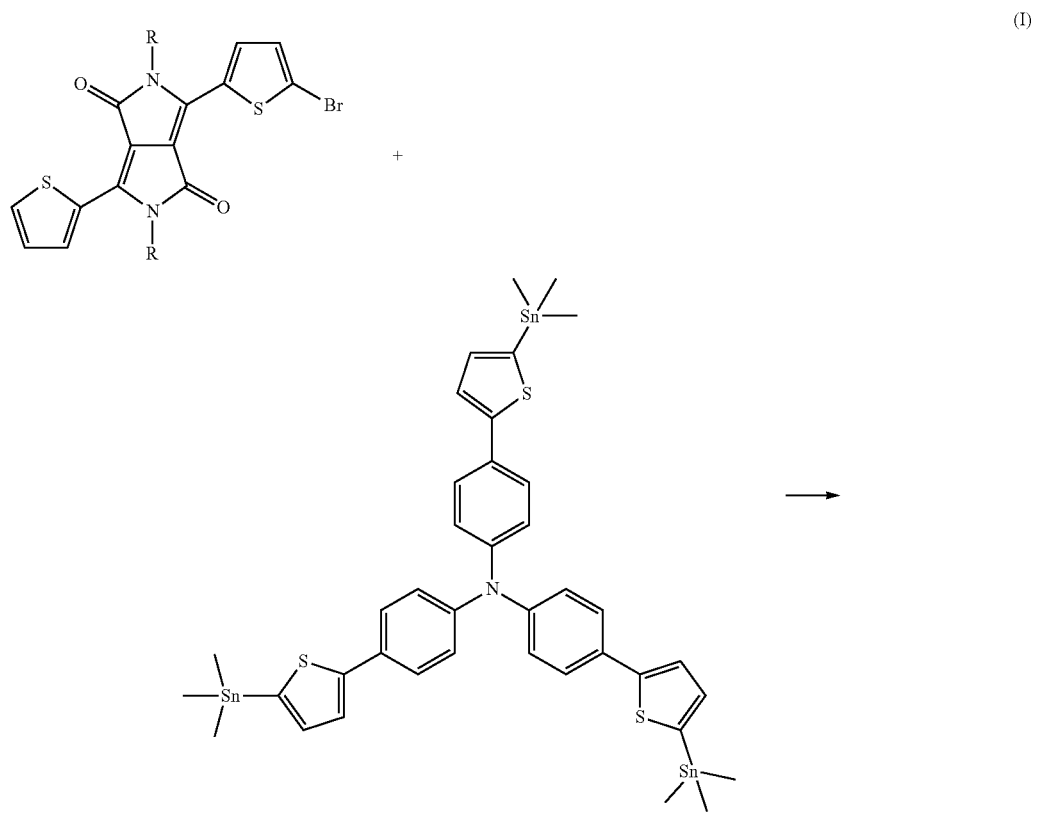

-continued

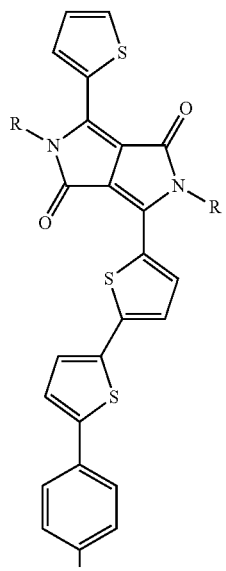

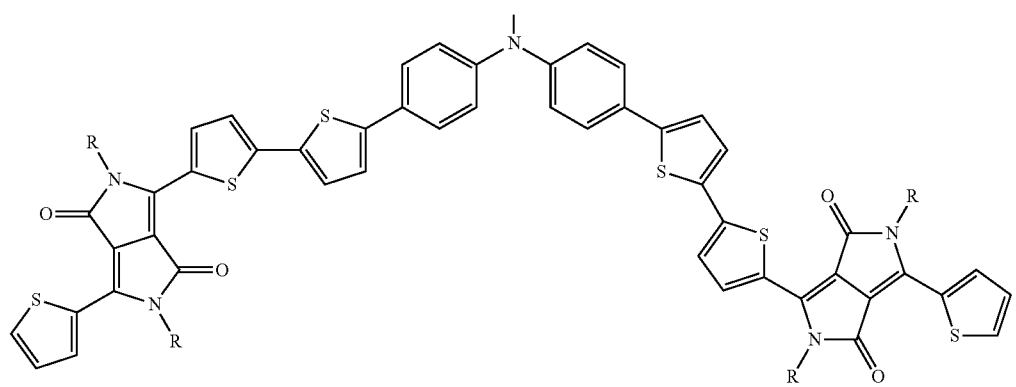

wherein each R is a 2-ethylhexyl or 2-butyloctyl group. The reaction is preferably carried out in the presence of bis(triphenylphosphine)palladium (II) dichloride ($PdCl_2(PPh_3)_2$) as a catalyst.

According to yet another aspect of the present invention, there is provided an organic photovoltaic cell including a photoactive layer using the triphenylamine derivative represented by Formula (1). The photoactive layer may further include a fullerene derivative.

The triphenylamine derivative of the present invention has a low band gap over a broad light-absorbing range, a high hole mobility and an appropriate molecular level. In addition, the organic photovoltaic cell including a photoactive layer using the triphenylamine derivative has very high efficiency.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
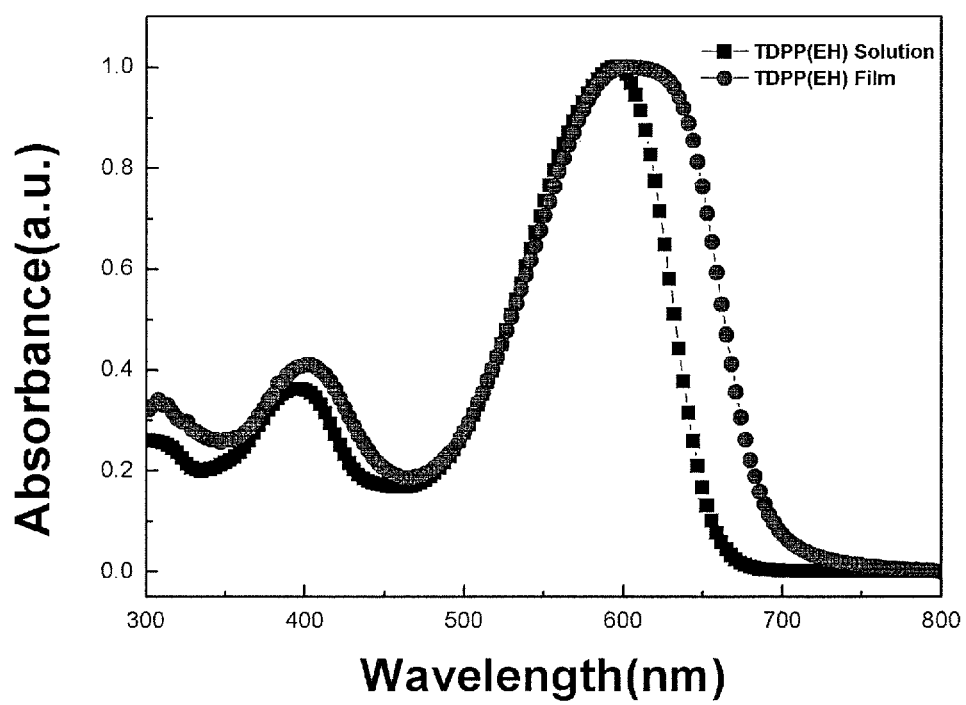
FIG. 1 shows absorbance curves for a solution and a film of TDPP(EH) prepared in Synthesis Example 7 of the present invention.

Embodiments of the present invention will now be described in more detail.

The present inventors have succeeded in synthesizing novel compounds with low band gaps from thiophene monomers and diketopyrrolopyrrole monomers, which were reported to have high hole mobilities and high absorbance values, and triphenylamine core structures with high hole conductivities, and in acquiring high photovoltaic efficiency of organic thin-film photovoltaic cells using the novel compounds.

The present invention provides a triphenylamine derivative represented by Formula (I):

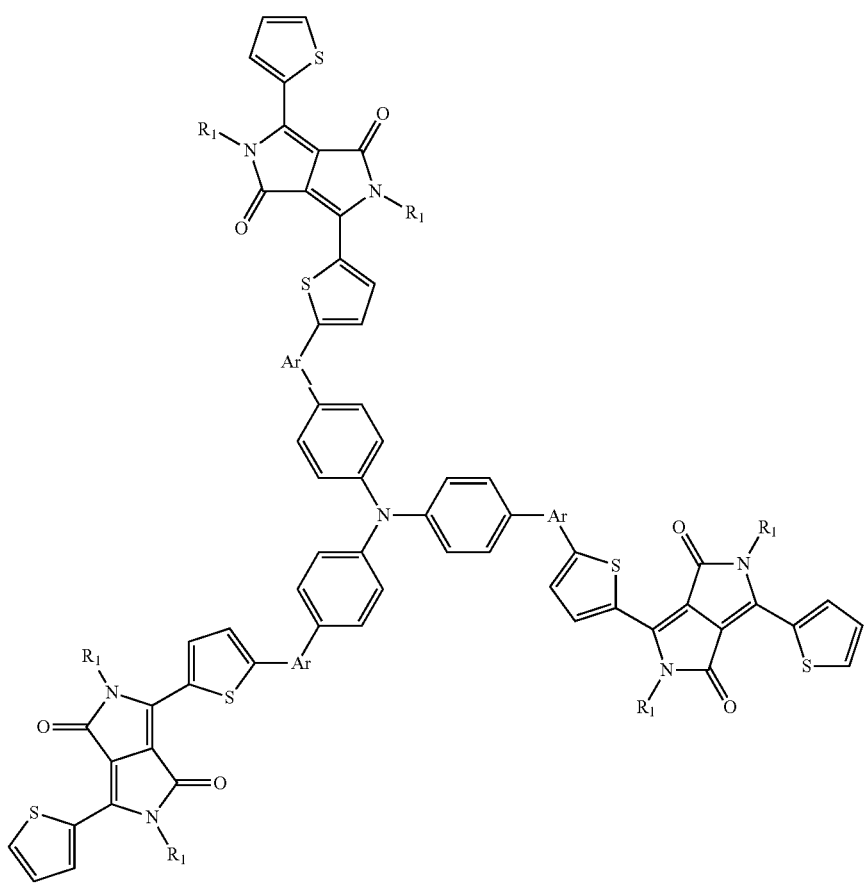
(I)
wherein the R₁ groups, which may be the same or different, each independently represent a straight or branched, saturated or unsaturated $C_1$-$C_{20}$ alkyl group, and the Ar moieties, which may be the same or different, each independently represent a linking group selected from
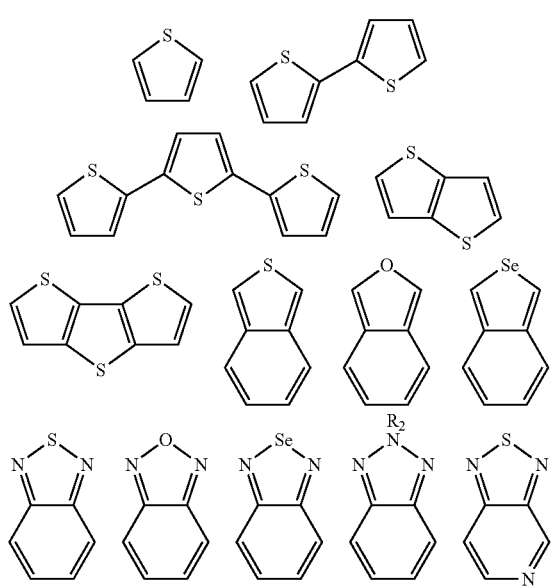
-continued
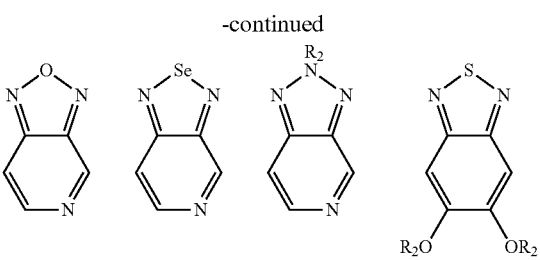
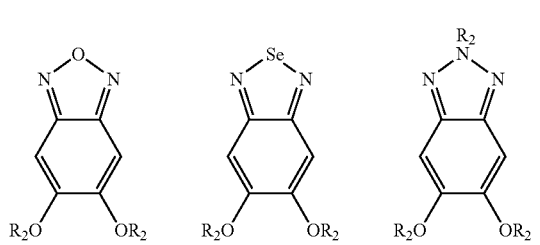
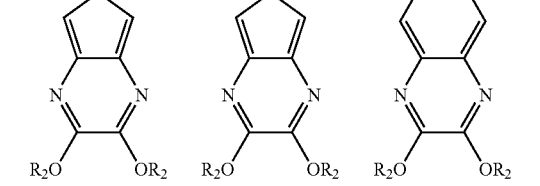

13
-continued

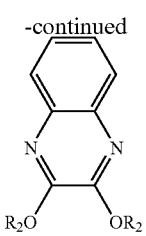

14 wherein the $R_2$ groups, which may be the same or different, each independently represent a straight or branched, saturated or unsaturated $C_1$-$C_{20}$ alkyl group.

The present invention will be explained in more detail with reference to the following examples. However, these examples are given to assist in a further understanding of the invention and are not to be construed as limiting the scope of the invention.

<Reaction Scheme 1>

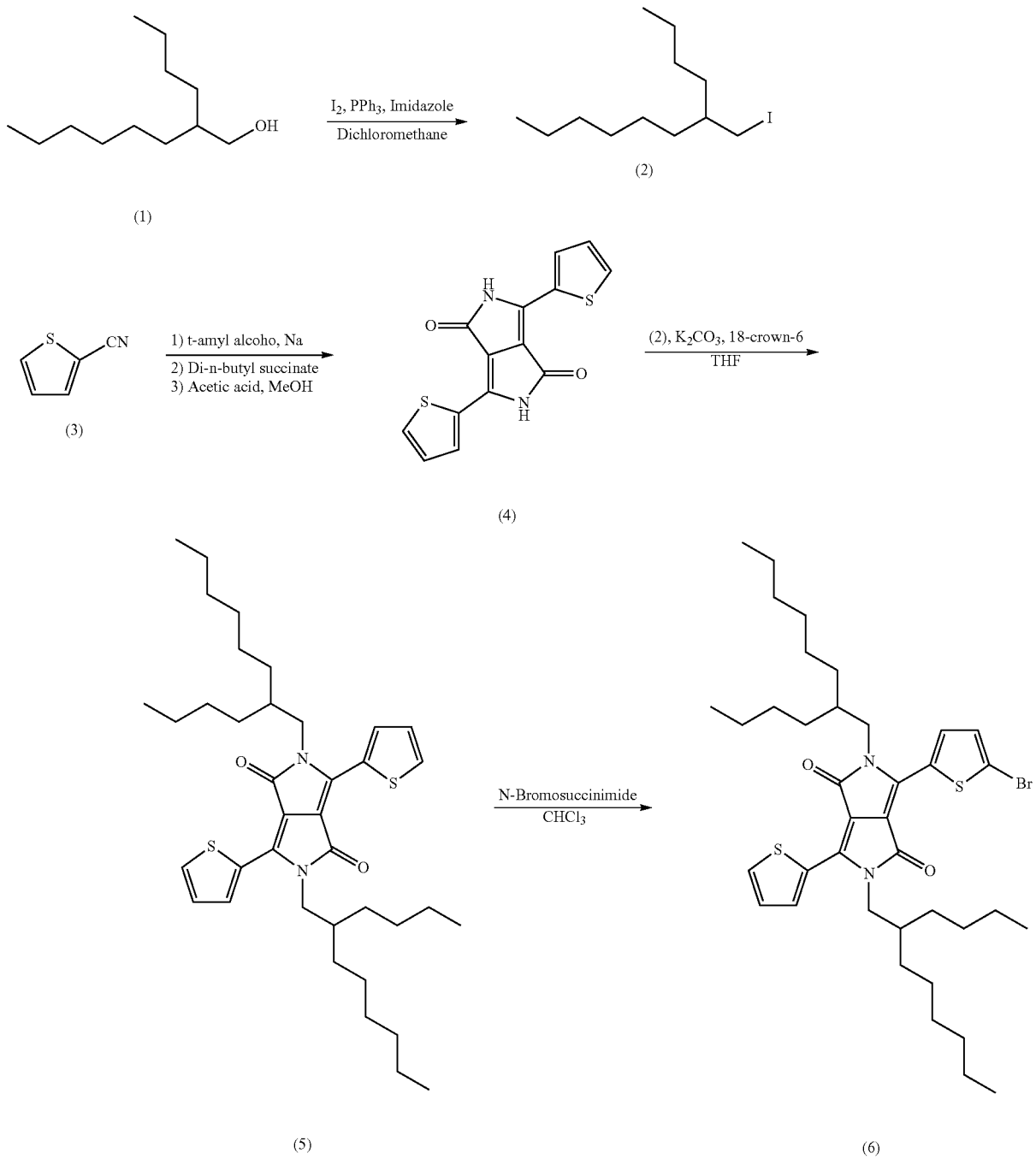

<Reaction Scheme 2>
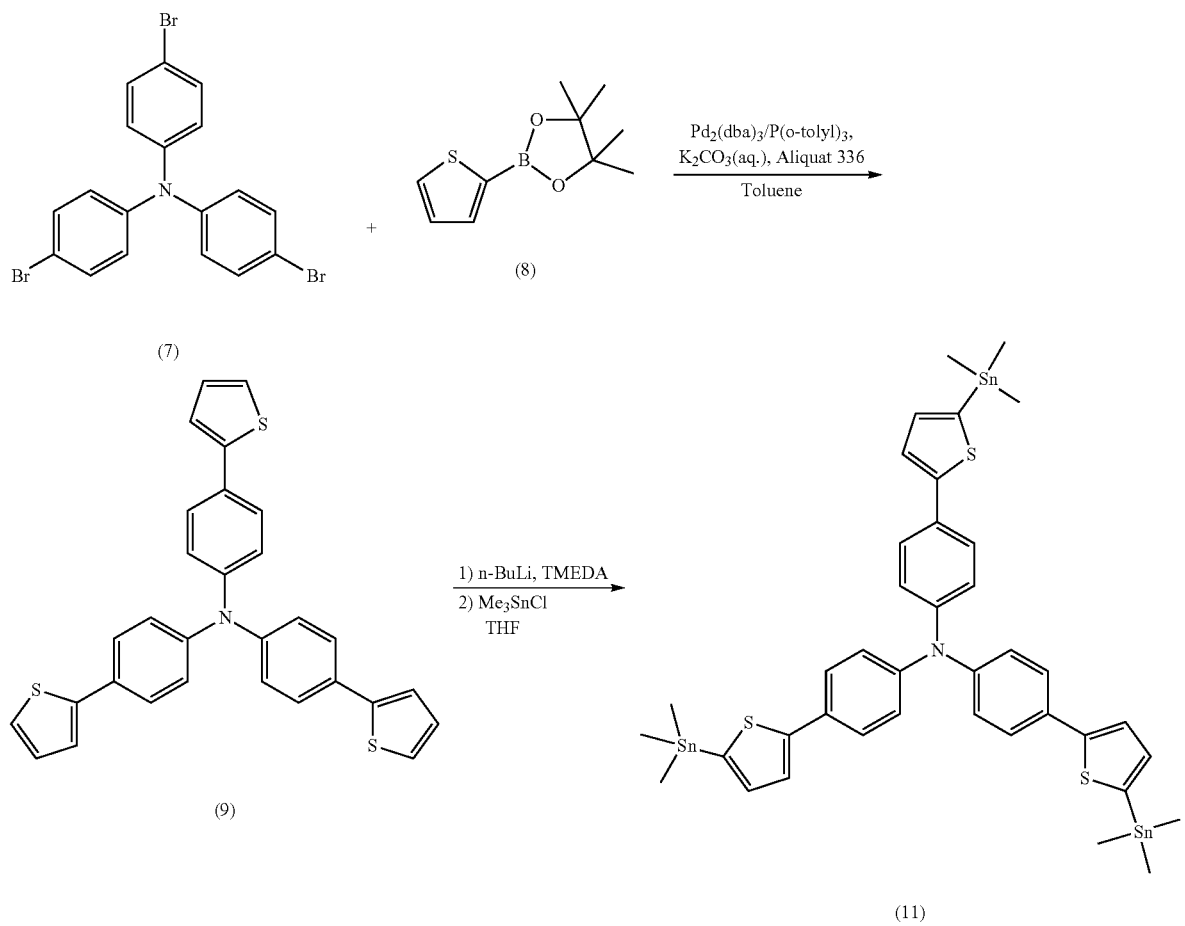
<Reaction Scheme 3>
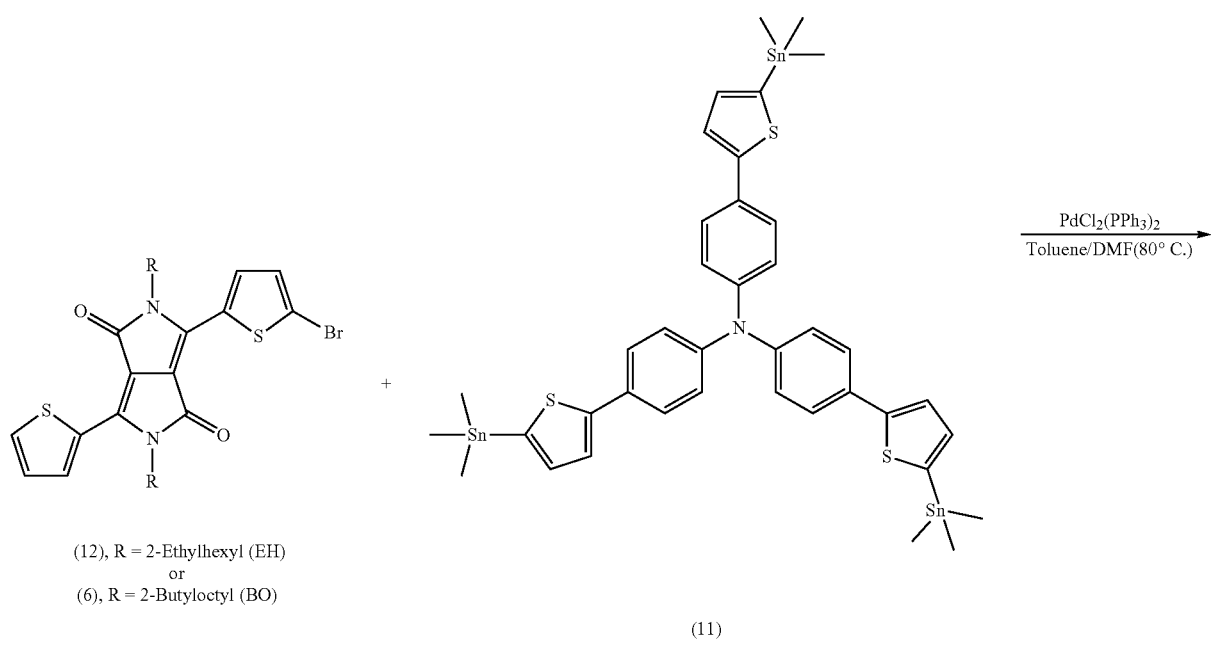

-continued

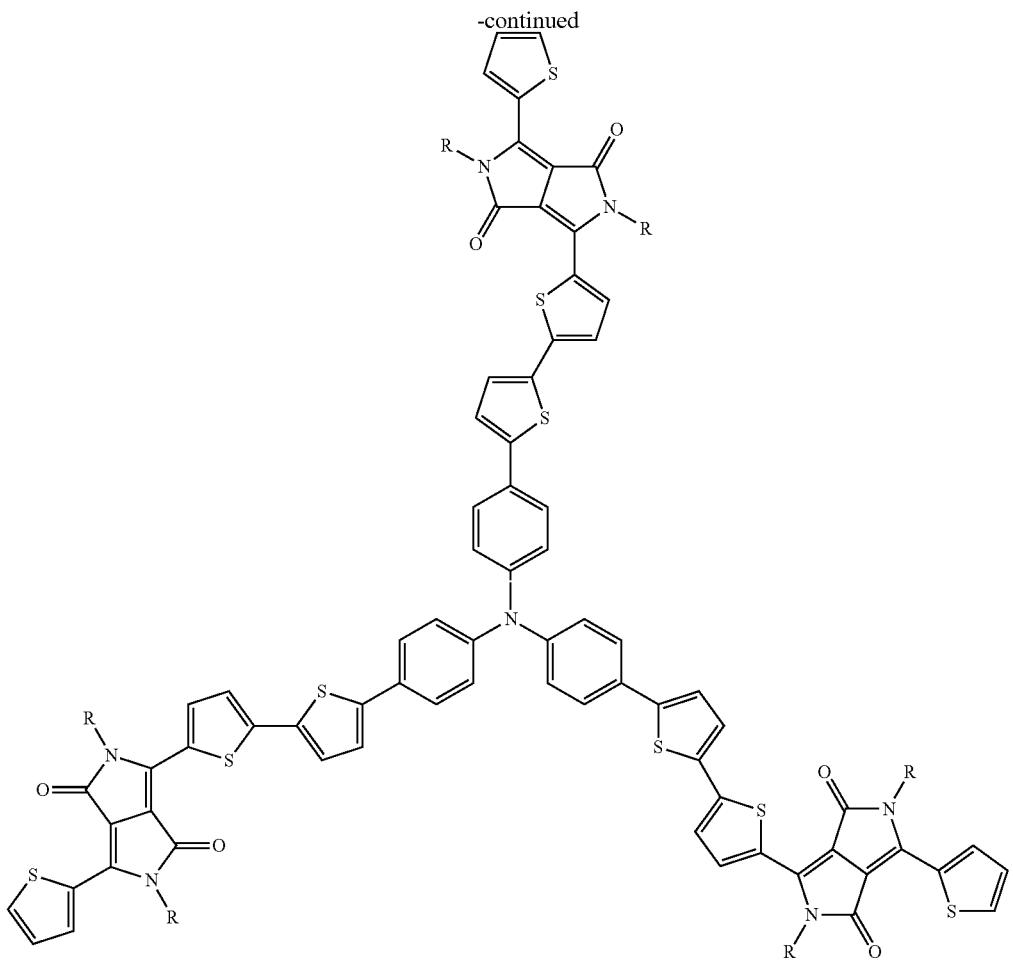

TDPP(EH), R = 2-Ethylhexyl
TDPP(BO), R = 2-Butyloctyl

Compounds (1), (3), (7), (8) and (12) shown in the reaction schemes were purchased from Aldrich or Lumtec.

Synthesis Example 1

Synthesis of 5-(iodomethyl)undecane (Formula 2)

2-Butyl-1-octanol (Formula 1) (6.4 ml, 28.6 mmol), triphenylamine (15.0 g, 57.2 mmol) and imidazole (3.89 g, 57.2 mmol) were placed in dichloromethane (210 ml) as a solvent in a 500 ml flask furnished with a magnetic stirring bar. The mixture was cooled to 0° C. After slow addition of iodine (14.52 g, 57.2 mmol) and slow heating to room temperature, the resulting mixture was allowed to react about 2 hr. After completion of the reaction, a saturated aqueous solution of sodium sulfite was added until no precipitate was observed. The reaction mixture was extracted with water and chloroform. The chloroform layer was dried over magnesium sulfate and the solvents were removed using a rotary evaporator. The residue was purified by column chromatography (eluent=hexane) to afford 8.0 g (yield=95%) of 5-(iodomethyl)undecane (Formula 2).

$^1$H-NMR (CDCl$_3$, δ ppm) 0.88 (t, 6H), 1.23 (m, 17H), 3.24 (d, 2H)

Synthesis Example 2

Synthesis of 3,6-di(thiophen-2-yl)pyrrolo[3,4-c]pyrrole-1,4(2H,5H)-dione (Formula 4)

t-amyl alcohol (250 ml) was placed in a 500 ml flask equipped with a magnetic stirring bar and a condenser. After heating to 60° C., sodium pieces were slowly added. The reaction was allowed to proceed at 120° C. for about 12 hr. Thereafter, 2-thiophenecarbonitrile (Formula 3) (10.0 ml, 107.4 mmol) and di-n-butylsuccinate (12.6 ml, 53.69 mmol) were slowly added. The mixture was allowed to react at 120° C. for about 12 hr. The reaction mixture was cooled, and acetic acid (11.2 ml, 195.7 mmol) and methanol (7.7 ml, 134.2 mmol) were added thereto. After reaction at room temperature for about 30 min, the reaction mixture was left to stand at room temperature for about 30 min to give a precipitate. The precipitate was filtered and dried under vacuum to afford 8.2 g (yield=51%) of 6-di(thiophen-2-yl)pyrrolo[3,4-c]pyrrole-1,4(2H,5H)-dione (Formula 4).

$^1$H-NMR (DMSO, δ ppm) 4.85 (dd, 2H), 5.51 (d, 2H, aromatic proton), 5.76 (d, 2H, aromatic proton), 8.79 (s, 2H, —NH—)

Synthesis Example 3

Synthesis of 2,5-bis(2-butyloctyl)-3,6-di(thiophen-2-yl)pyrrolo[3,4-c]pyrrole-1,4(2H,5H)-dione (Formula 5)

6-Di(thiophen-2-yl)pyrrolo[3,4-c]pyrrole-1,4(2H,5H)-dione (Formula 4) (0.59 g, 1.96 mmol) prepared in Synthesis Example 2 and 5-(iodomethyl)undecane (Formula 2) (1.75 g, 5.89 mmol) prepared in Synthesis Example 1 were placed in a 500 ml flask equipped with a magnetic stirring bar and a condenser. The mixture was dissolved in dimethylformamide (30 ml) as a solvent. The reaction was allowed to proceed at 140° C. for about 12 hr. After completion of the reaction, the reaction solution was slowly cooled to room temperature to obtain a precipitate. The precipitate was collected by filtration to remove the solvent, followed by extraction with ether and water. Purification by column chromatography (eluent=chloroform/hexane (1:1)) afforded 0.6 g (yield=45%) of 2,5-bis(2-butyloctyl)-3,6-di(thiophen-2-yl)pyrrolo[3,4-c]pyrrole-1,4(2H,5H)-dione (Formula 5).

$^1$H-NMR (CDCl$_3$, δ ppm) 0.84 (t, 6H), 1.24 (m, 64H), 1.90 (m, 2H), 4.02 (d, 4H), 7.26 (dd, 2H, aromatic proton), 7.62 (d, 2H, aromatic proton), 8.85 (d, 2H, aromatic proton)

Synthesis Example 4

Synthesis of 3-(5-bromothiophen-2-yl)-2,5-bis(2-butyloctyl)-6-(thiophen-2-yl)pyrrolo[3,4-c]pyrrole-1,4(2H,5H)-dione (Formula 6)

2,5-Bis(2-butyloctyl)-3,6-di(thiophen-2-yl)pyrrolo[3,4-c]pyrrole-1,4(2H,5H)-dione (Formula 5) (1.17 g, 1.84 mmol) was dissolved in chloroform (40 ml) as a solvent in a 100 ml flask furnished with a magnetic stirring bar. The solution was cooled to 0° C. Thereafter, a solution of N-bromosuccinimide (0.34 g, 1.93 mmol) in chloroform (20 ml) as a solvent was slowly added dropwise to the flask through a dropping funnel. The reaction was allowed to proceed for about 2 hr. The reaction mixture was extracted with chloroform and water. The chloroform layer was collected and the solvent was removed using a rotary evaporator. The residue was purified by column chromatography (eluent=dichloromethane/hexane (1:1)) to afford 0.6 g (yield=45%) of 3-(5-bromothiophen-2-yl)-2,5-bis(2-butyloctyl)-6-(thiophen-2-yl)pyrrolo[3,4-c]pyrrole-1,4(2H,5H)-dione (Formula 6).

$^1$H-NMR (CDCl$_3$, δ ppm) 0.84 (t, 6H), 1.24 (m, 64H), 1.90 (m, 2H), 4.02 (d, 4H), 7.22 (d, 1H, aromatic proton), 7.26 (dd, 1H, aromatic proton), 7.62 (d, 1H, aromatic proton), 8.59 (d, 1H, aromatic proton), 8.85 (d, 1H, aromatic proton)

Synthesis Example 5

Synthesis of tris(4-(thiophen-2-yl)phenyl)amine (Formula 9)

Anhydrous toluene (20 ml) as a solvent was placed in a 100 ml flask equipped with a magnetic stirring bar and a condenser, and then tris(4-bromophenyl)amine (1.0 g, 2.1 mmol) (Formula 7), 4,4,5,5-tetramethyl-2-(thiophen-2-yl)-1,3,2-dioxaborolane (1.7 g, 7.88 mmol) (Formula 8), dipalladiumtris(dibenzylacetone) (Pd$_2$(dba)$_3$) (0.1 g, 0.11 mmol), tri-o-tolyl phosphate (P(o-tolyl)$_3$) (0.2 g, 0.4 mmol), potassium carbonate (K$_2$CO$_3$) (1.1 g, 8.3 mmol) and trioctylmethylammonium chloride (Aliquat 336) (1 drop) were added thereto. After oxygen was removed from the flask by vacuum-nitrogen cycling, the mixture was stirred at reflux under a nitrogen atmosphere at 85° C. for 48 hr. The stirring was stopped, and the toluene layer was collected, filtered through a short column (eluent=chloroform), and dried. The residue was purified by column chromatography (eluent=dichloromethane/hexane (1:1)) to afford 0.88 g (yield=86%) of tris(4-(thiophen-2-yl)phenyl)amine (Formula 9).

$^1$H-NMR (CDCl$_3$, δ ppm) 7.07 (dd, 3H, aromatic proton), 7.13 (d, 6H, aromatic proton), 7.24 (m, 6H, aromatic proton), 7.52 (d, 6H, aromatic proton)

Synthesis Example 6

Synthesis of tris(4-(5-trimethylstannyl yl)phenyl)amine (Formula 11)

Tris(4-(thiophen-2-yl)phenyl)amine (Formula 9) (0.1 g, 0.203 mmol) was placed in a 25 ml flask furnished with a magnetic stirring bar. Flame drying was conducted to remove moisture from the flask, followed by vacuum-nitrogen cycling to create a nitrogen atmosphere in the flask. Anhydrous tetrahydrofuran (THF) (5 ml) as a solvent was added to the flask. The mixture was cooled to −78° C., and then n-butyllithium (0.05 g, 0.8 mmol) and tetramethylethylenediamine (0.1 mg, 0.8 mmol) were slowly added thereto. After slow heating to room temperature, the reaction was continued for 2 hr. The reaction mixture was cooled to −78° C., and then trimethyltin chloride (SnMe$_3$Cl) (0.2 g, 0.8 mmol) was added thereto. The temperature was allowed to rise to room temperature. The resulting mixture was allowed to react for 8 hr. The reaction mixture was extracted with water and ether. The ether layer was collected and the solvents were removed using a rotary evaporator. The residue was reprecipitated in chloroform and methanol, and dried in vacuo to afford 70 mg (yield=35%) of tris(4-(5-trimethylstannyl)thiophen-2-yl)phenyl)amine (Formula 11).

$^1$H-NMR (CDCl$_3$, δ ppm) 7.12 (d, 6H, aromatic proton), 7.15 (d, 3H, aromatic proton), 7.34 (d, 3H, aromatic proton), 7.52 (d, 611, aromatic proton)

Synthesis Example 7

Synthesis of triphenyl derivative TDPP(EH) (Formula Ia)

3-(5-Bromothiophen-2-yl)-2,5-bis(2-ethylhexyl)-6-(thiophen-2-yl)pyrrolo[3,4-c]pyrrole-1,4(2H,5H)-dione (Formula 12) (1044.8 mg, 1.35 mmol) and tris(4-(5-trimethylstannyl)thiophen-2-yl)phenyl)amine (Formula 11) (487.2 mg, 0.41 mmol) were placed in a 25 ml flask furnished with a magnetic stirring bar, and then toluene (40 ml) and dimethylformamide (10 ml) as solvents were added thereto. Oxygen was removed from the flask by degassing. Bis(triphenylphosphine)palladium(II)dichloride (PdCl$_2$(PPh$_3$)$_2$) (15.1 mg 0.016 mmol) as a catalyst was added, followed by heating to 80° C. The reaction was allowed to react for about 4 hr. The reaction mixture was cooled to room temperature, reprecipitated in methanol (150 ml), and filtered to obtain a dark brown solid. The solid was dissolved in chloroform and purified by column chromatography (eluent=dichloromethane/hexane (2:1)) to afford 650 mg (yield=77%) TDPP(EH) (Formula Ia) as the final product in the form of a black powder.

$^1$H-NMR (CDCl$_3$, δ ppm) 0.88 (m, 36H), 1.25 (m, 48H), 4.04 (d, 12H), 7.18 (d, 6H, aromatic proton), 7.24 (dd, 3H, aromatic proton), 7.27 (d, 3H, aromatic proton), 7.31 (d, 3H, aromatic proton), 7.33 (d, 3H, aromatic proton), 7.55 (d, 6H, aromatic proton), 7.62 (d, 3H, aromatic proton), 8.85 (d, 3H, aromatic proton), 8.94 (d, 3H, aromatic proton)

Synthesis Example 8

Synthesis of triphenyl TDPP(BO) (Formula Ib)

3-(5-Bromothiophen-2-yl)-2,5-bis(2-butyloctyl)-6-(thiophen-2-yl)pyrrolo[3,4-c]pyrrole-1,4(2H,5H)-dione (Formula 6) (288.0 mg, 0.40 mmol) and tris(4-(5-trimethylstannyl)thiophen-2-yl)phenyl)amine (Formula 11) (119.5 mg, 0.12 mmol) were placed in a 25 ml flask furnished with a magnetic stirring bar, and then toluene (8 ml) and dimethylformamide (2 ml) as solvents were added thereto. Oxygen was removed from the flask by degassing. Bis(triphenylphosphine)palladium(II)dichloride(PdCl$_2$(PPh$_3$)$_2$) (3.4 mg, 0.005 mmol) as a catalyst was added, followed by heating to 80° C. The mixture was allowed to react for about 4 hr. The reaction mixture was cooled to room temperature, reprecipitated in methanol (150 ml), and filtered to obtain a dark brown solid. The solid was dissolved in chloroform and purified by column chromatography (eluent=dichloromethane/hexane (2:1)) to afford 201 mg (yield=68%) of TDPP(BO) (Formula Ib) as the final product in the form of a black powder.

$^1$H-NMR (CDCl$_3$, δ ppm) 0.88 (m, 36H), 1.25 (m, 90H), 4.04 (d, 12H), 7.18 (d, 6H, aromatic proton), 7.24 (dd, 3H, aromatic proton), 7.27 (d, 3H, aromatic proton), 7.31 (d, 3H, aromatic proton), 7.33 (d, 3H, aromatic proton), 7.55 (d, 6H, aromatic proton), 7.62 (d, 3H, aromatic proton), 8.85 (d, 3H, aromatic proton), 8.94 (d, 3H, aromatic proton)

Example 1

Fabrication of Photovoltaic Cells Using Triphenylamine Derivatives

Each of the triphenylamine derivative TDPP(EH) (Formula Ia) prepared in Synthesis Example 7 and the triphenylamine derivative TDPP(BO) (Formula Ib) prepared in Synthesis Example 8 was used to fabricate a photovoltaic cell having a structure of ITO/PEDOT:PSS/triphenylamine derivative:PC$_{70}$BM (1:3.5)/Al in accordance with the following procedure. First, an ITO substrate was sequentially washed with isopropyl alcohol for 10 min, acetone for 10 min and isopropyl alcohol for 10 min, and dried before use. A solution of PEDOT:PSS in a ratio of 1:1 was diluted in methanol, spin coated at a rate of 4,000 rpm on the ITO substrate, and dried at 110° C. for 10 min. The triphenylamine derivative and PC$_{70}$BM were dissolved in a ratio of 1:3.5 in chloroform to prepare a solution having a concentration of 15 mg/ml. The solution was spin coated at a rate of 2,500 rpm on the substrate, and an aluminum electrode was deposited to a thickness of 100 nm thereon.

Evaluation Example 1

Characterization of Photovoltaic Cells

Figure 2:
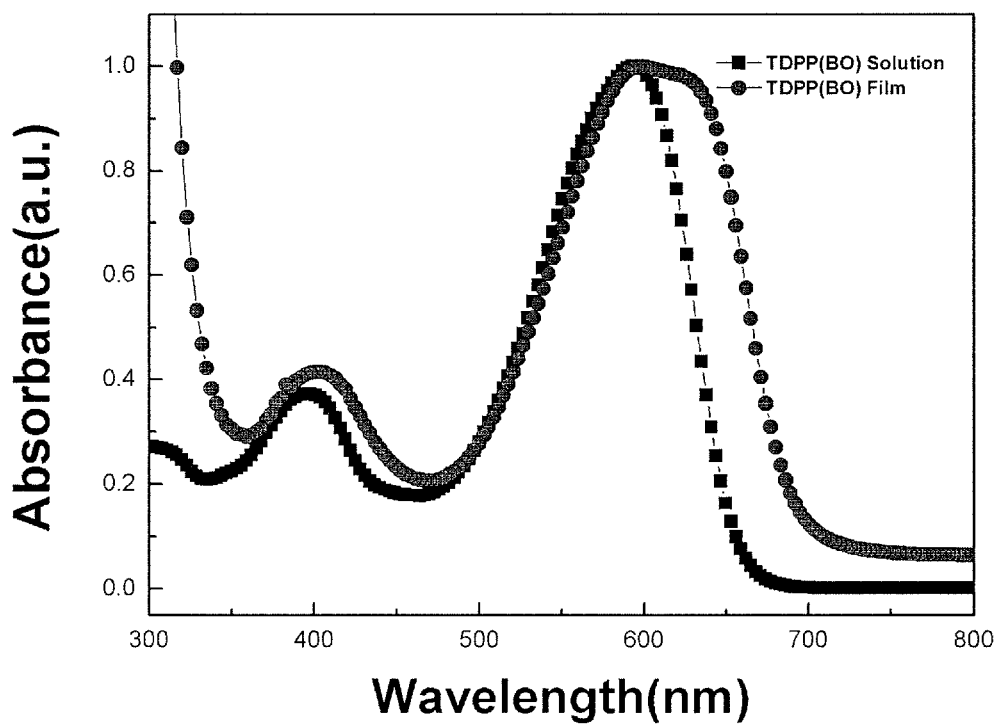
FIG. 2 shows absorbance curves for a solution and a film of TDPP(BO) prepared in Synthesis Example 8 of the present invention.

FIGS. 1 and 2 are absorbance curves for solutions and films of TDPP(EH) (Formula Ia) prepared in Synthesis Example 7 and TDPP(BO) (Formula Ib) prepared in Synthesis Example 8, respectively. The maximum absorbance values and optical band gaps of the solutions and the films were determined from the absorbance data, and the results are shown in Table 1. From these results, it can be seen that the triphenylamine derivatives having low band gaps are suitable for use in the fabrication of high efficiency organic photovoltaic cells.

TABLE 1

| | Solution ($\lambda_{max}$, nm) | Solution ($\lambda_{onset}$, nm) | Film ($\lambda_{onset}$, nm) | Optical band gap ($E_{g,opt}$, eV) |
|---|---|---|---|---|
| TDPP(EH) | 596 | 665 | 700 | 1.77 |
| TDPP(BO) | 593 | 665 | 700 | 1.77 |

Figure 3:
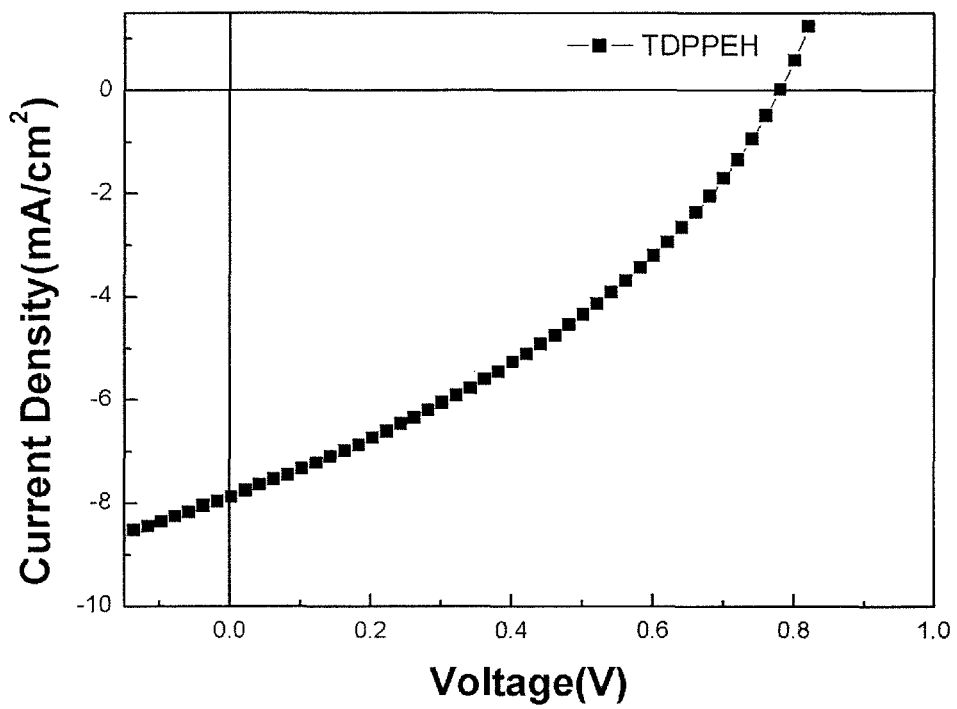
FIG. 3 is a curve showing the current density-voltage (J-V) characteristics of TDPP(EH) prepared in Synthesis Example 7 of the present invention.
Figure 4:
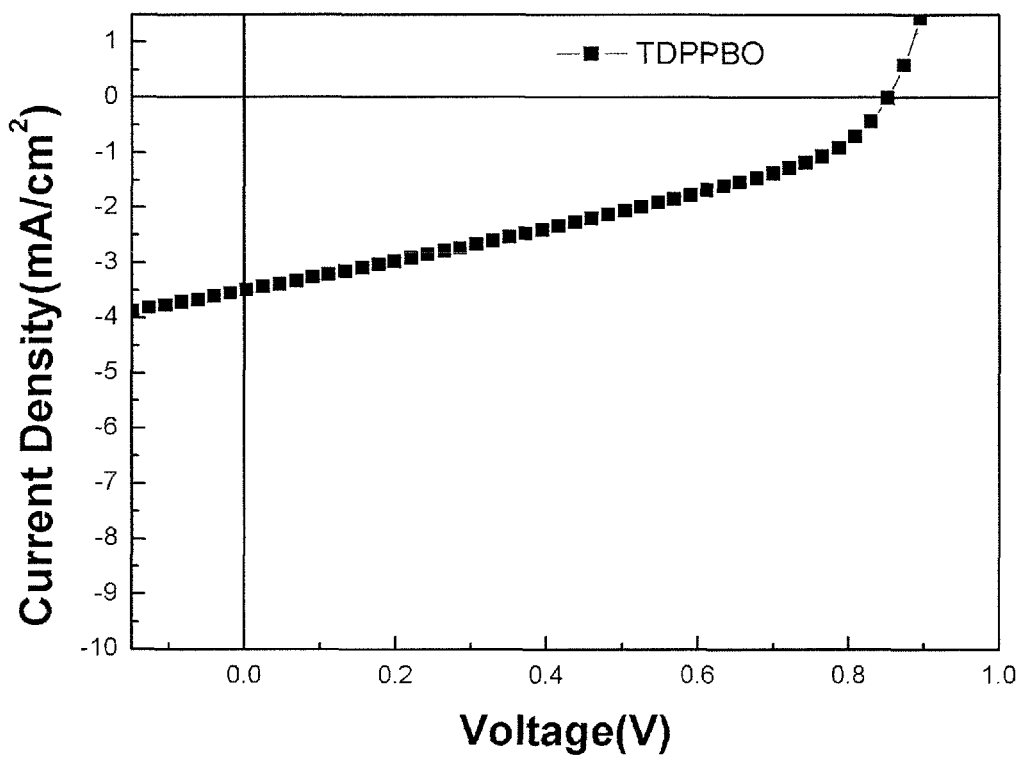
FIG. 4 is a curve showing the current density-voltage (J-V) characteristics of TDPP(BO) prepared in Synthesis Example 8 of the present invention.

The characteristics of the photovoltaic cells were measured, and the results are shown in FIGS. 3 and 4. Main parameters indicating the performance of the photovoltaic cells for the curves of FIGS. 3 and 4 are described in Table 2.

TABLE 2

| | $V_{oc}$ (V) | $J_{sc}$ (mA/cm$^2$) | FF | PCE (%) |
|---|---|---|---|---|
| TDPP(EH) | 0.78 | 7.90 | 0.36 | 2.2 |
| TDPP(BO) | 0.85 | 3.50 | 0.35 | 1.1 |

What is claimed is:
1. A triphenylamine derivative represented by Formula (I):

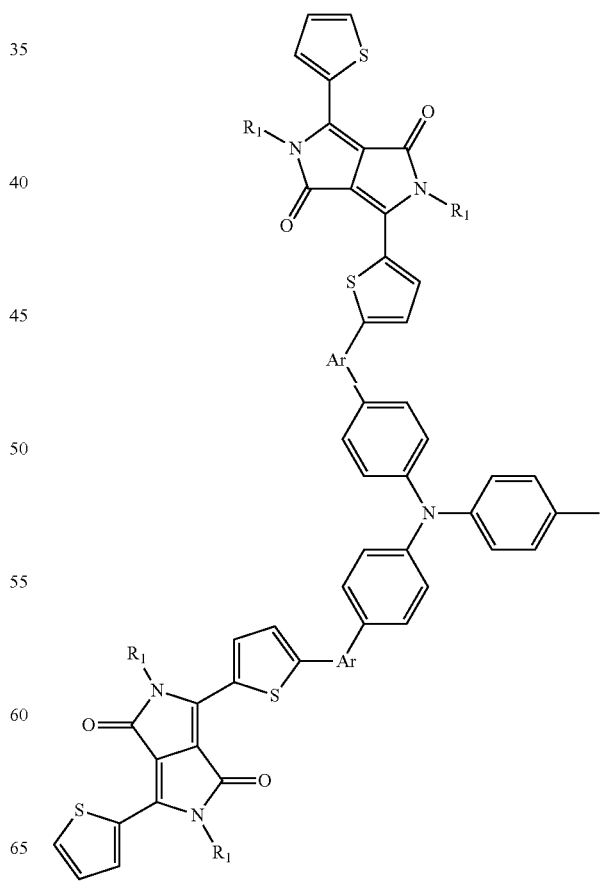

(I)

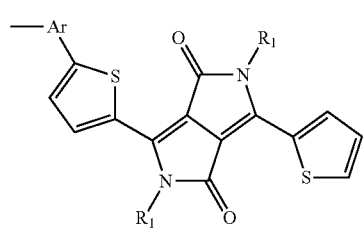

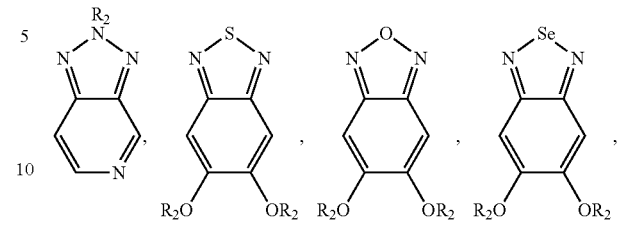

wherein the R1 groups, which are the same or different, each independently represent a straight or branched, saturated or unsaturated $C_1$-$C_{20}$ alkyl group, and the Ar moieties, which are the same or different, each independently represent a linking group selected from group consisting of

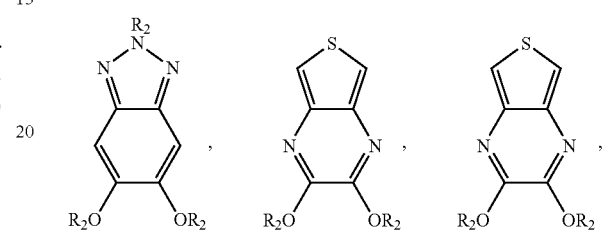

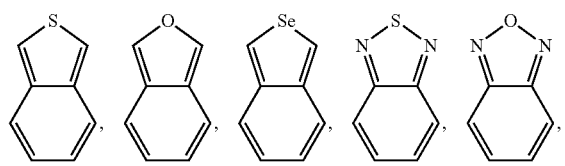

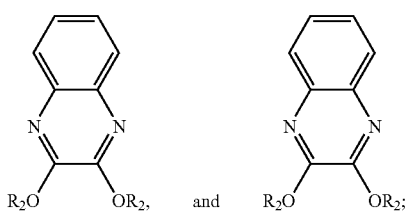

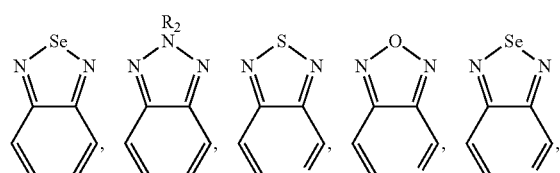

wherein the $R_2$ groups, which are the same or different, each independently represent a straight or branched, saturated or unsaturated $C_1$-$C_{20}$ alkyl group.

2. The triphenylamine derivative according to claim 1, wherein the triphenylamine derivative is a compound represented by Formula (Ia) or (Ib):

(Ia)

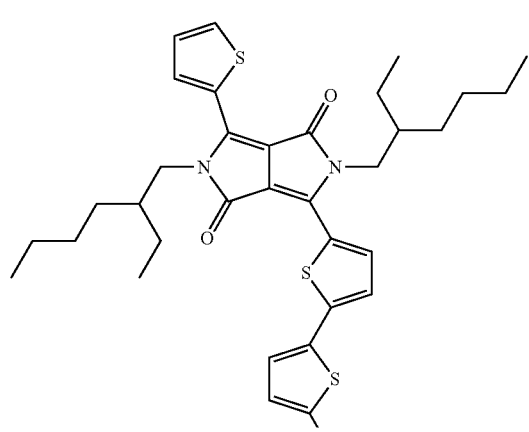

-continued
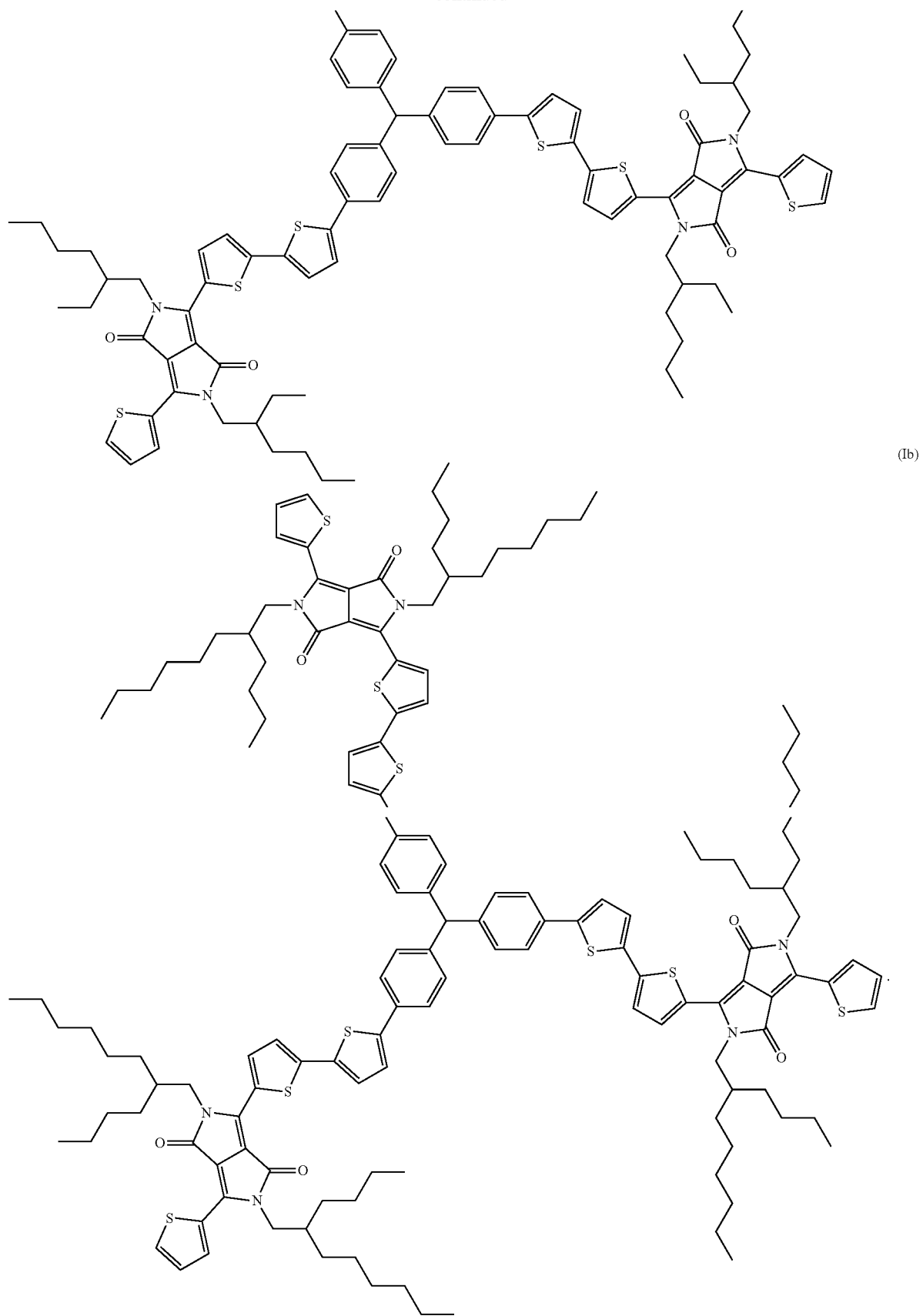
(Ib)

3. An organic photovoltaic cell comprising a photoactive layer comprising the triphenylamine derivative according to claim 1.

4. The organic photovoltaic cell according to claim 3, wherein the photoactive layer further comprises a fullerene derivative.

5. A method for preparing a triphenylamine derivative represented by Formula (I), comprising:

mixing a reaction mixture;

adding at least one solvent;

removing oxygen;

heating the reaction mixture; and cooling the reaction mixture, wherein the reaction is depicted in Reaction (I):

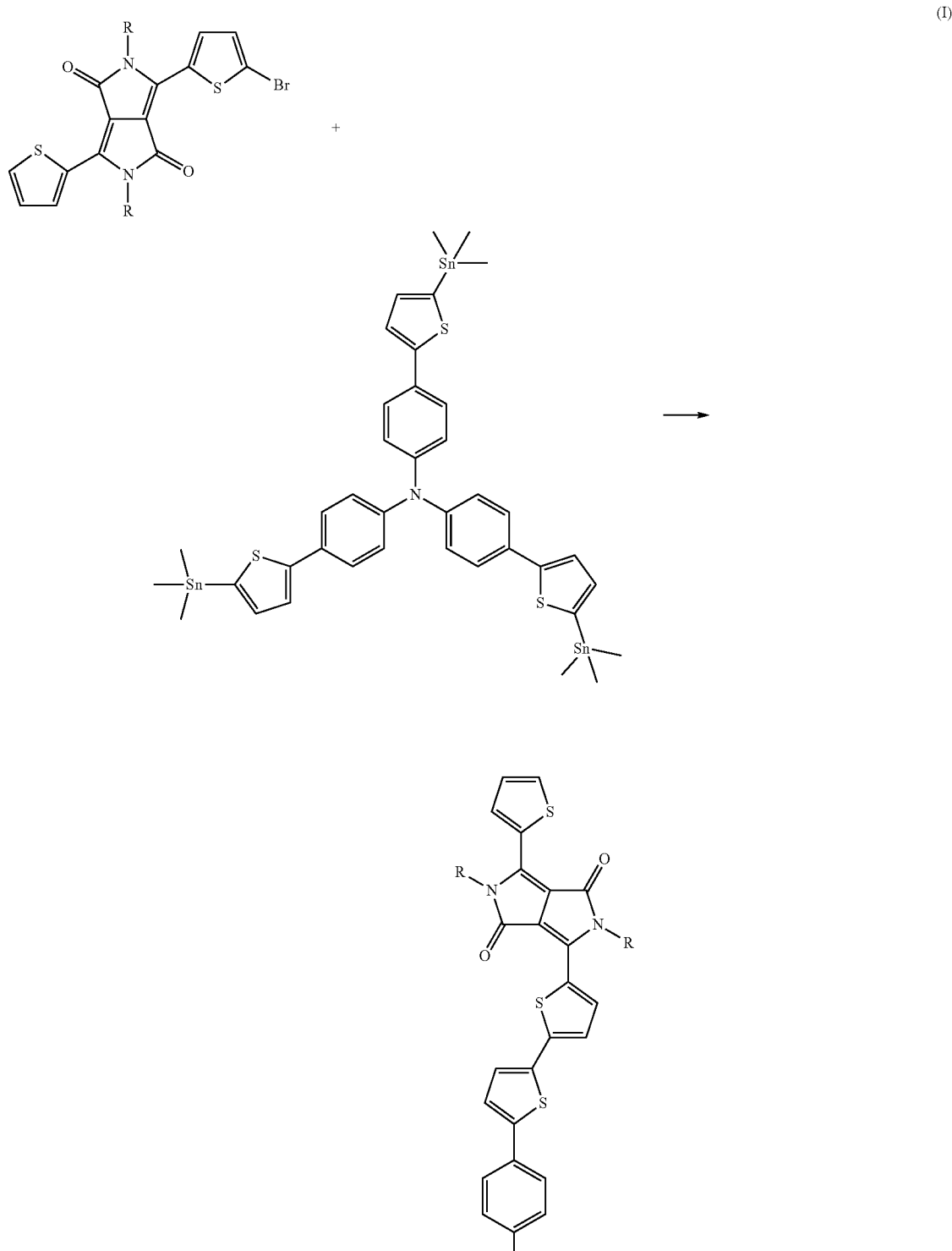

-continued

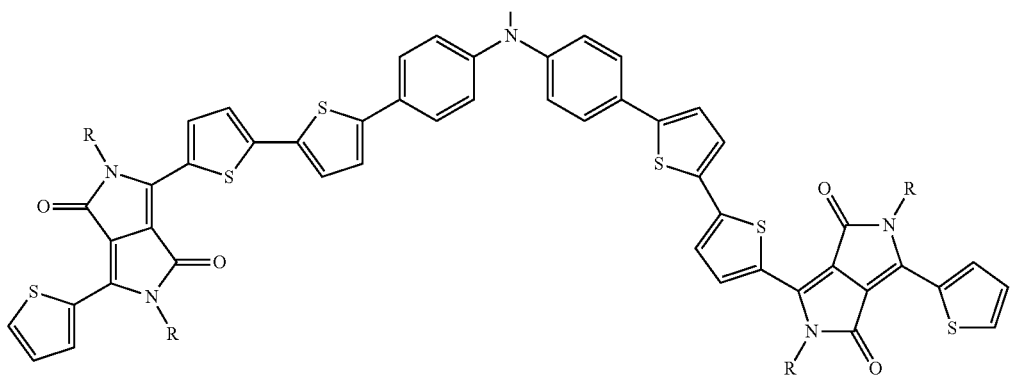

wherein each R is a 2-ethylhexyl or 2-butyloctyl group.

6. The method according to claim 5, wherein the reaction is carried out in the presence of bis(triphenylphosphine)palladium (II) dichloride ($PdCl_2(PPh_3)_2$) as a catalyst.

7. A method for preparing a triphenylamine derivative represented by Formula (I), comprising:
mixing a reaction mixture;
adding at least one solvent;
removing oxygen;
heating the reaction mixture; and
cooling the reaction mixture,
reprecipitating the reaction mixture;
filtering the reaction mixture to obtain a solid;
dissolving the solid; and
purifying the solid;
wherein the reaction is depicted in Reaction (I):

(I)

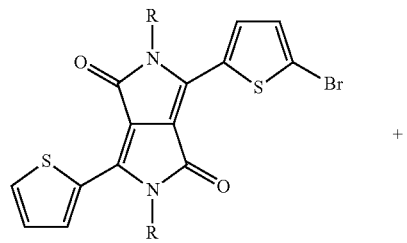

+

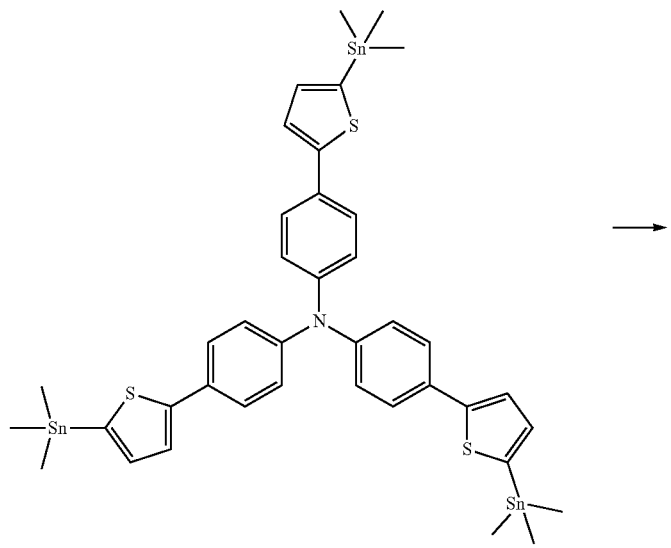

→

-continued
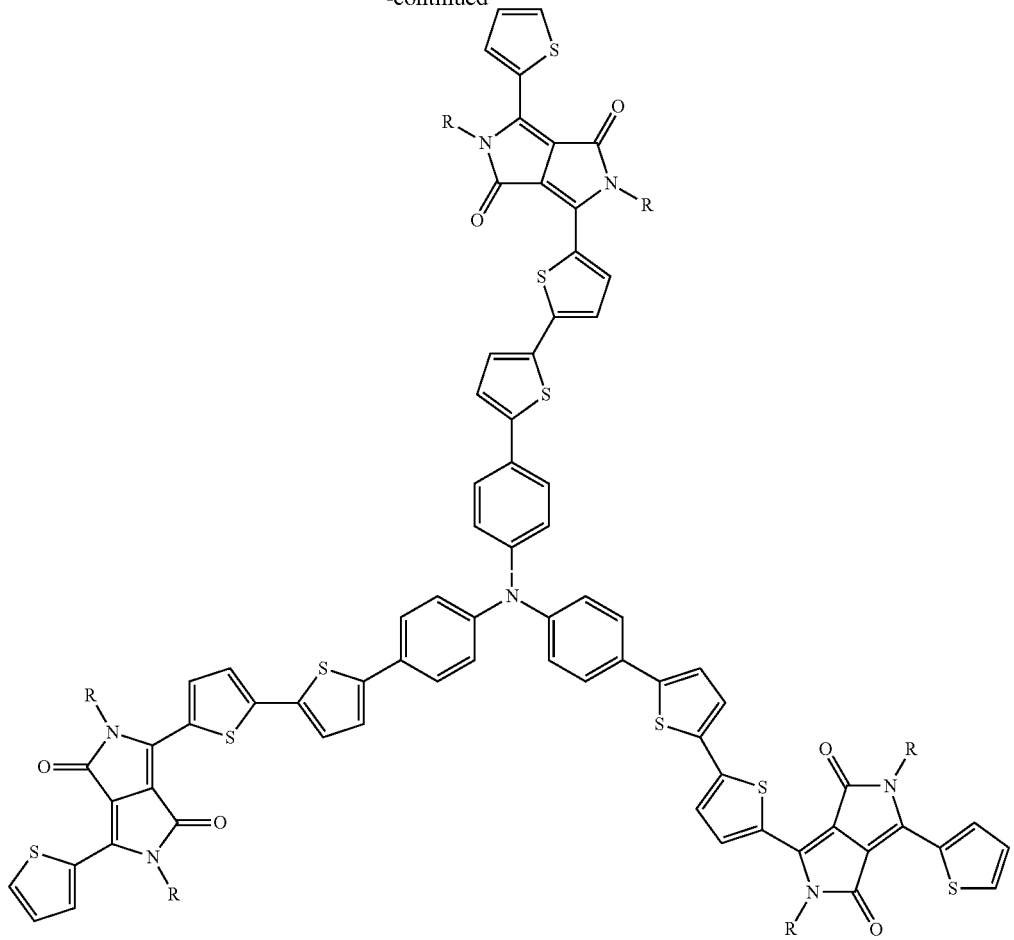
wherein each R is a 2-ethylhexyl or 2-butyloctyl group.
* * * * *